US009211329B2

(12) United States Patent
McKenzie et al.

(10) Patent No.: US 9,211,329 B2

(45) Date of Patent: Dec. 15, 2015

(54) METHOD OF TREATING INFLAMMATORY BOWEL DISEASE

(71) Applicant: CSL LIMITED, Victoria (AU)

(72) Inventors: Brent McKenzie, Parkville (AU); Eugene Maraskovsky, Parkville (AU)

(73) Assignee: CSL LIMITED, Parkville, Victoria (AU)

(*) Notice: Subject to any disclaimer, the term of this patent is extended or adjusted under 35 U.S.C. 154(b) by 0 days.

(21) Appl. No.: 13/724,450

(22) Filed: Dec. 21, 2012

(65) Prior Publication Data

US 2013/0164291 A1 Jun. 27, 2013

Related U.S. Application Data

(60) Provisional application No. 61/579,555, filed on Dec. 22, 2011.

(51) Int. Cl.

| | |
|---|---|
| ***A61K 39/395*** | (2006.01) |
| ***A61K 31/7088*** | (2006.01) |
| ***C07K 16/24*** | (2006.01) |
| ***A61K 31/7105*** | (2006.01) |
| ***A61K 31/713*** | (2006.01) |
| *A61K 39/00* | (2006.01) |

(52) U.S. Cl.

CPC ......... *A61K 39/3955* (2013.01); *A61K 31/7088* (2013.01); *A61K 31/713* (2013.01); *A61K 31/7105* (2013.01); *C07K 16/243* (2013.01); *A61K 2039/505* (2013.01)

(58) Field of Classification Search

CPC ....................... A61K 2039/505; A61K 39/395

See application file for complete search history.

(56) References Cited

U.S. PATENT DOCUMENTS

| | | | | |
|---|---|---|---|---|
| 5,747,032 | A * | 5/1998 | Metcalf et al. | 424/133.1 |
| 6,200,567 | B1 | 3/2001 | Lopez et al. | |
| 7,108,852 | B2 * | 9/2006 | Devalaraja et al. | 424/130.1 |
| 2004/0053365 | A1 | 3/2004 | Renner et al. | |
| 2006/0233797 | A1 * | 10/2006 | Gujrathi | 424/144.1 |
| 2008/0171038 | A1 | 7/2008 | Bebbington et al. | |
| 2008/0292641 | A1 | 11/2008 | Sass et al. | |
| 2008/0317757 | A1 | 12/2008 | Nakajima | |
| 2009/0053213 | A1 | 2/2009 | Steidl et al. | |
| 2009/0130093 | A1 | 5/2009 | Cohen et al. | |
| 2009/0274702 | A1 | 11/2009 | Hamilton et al. | |
| 2009/0274706 | A1 | 11/2009 | Bebbington et al. | |
| 2011/0189082 | A1 | 8/2011 | Kirchner et al. | |

FOREIGN PATENT DOCUMENTS

| | | |
|---|---|---|
| WO | WO 2006/111353 A2 | 10/2006 |
| WO | WO 2009/133103 A1 | 11/2009 |

OTHER PUBLICATIONS

Kelsen MD J.R. et al., "Phase I Trial of Sargramostim in Pediatric Crohn's Disease", Inflamm Bowel Dis 16 (7):1203-1208 (Jul. 2010).

Khajah M et al., "Granulocyte-Macrophage Colony-Stimulating Factor (GM-CSF): A Chemoattractive Agent for Murine Leukocytes In Vivo", Journal of Leukocyte Biology 89:945-953 (Jun. 2011).

Korzenik J.R. et al., "Sargramostim for Active Crohn's Disease", The New England Journal of Medicine 352:2193-2201 (May 26, 2005).

Sainathan, PHD S.K. et al., "Granulocyte Macrophage Colony-Stimulating Factor Ameliorates DSS-Induced Experimental Colitis", Inflamm Bowel Dis 14(1):88-99 (Jan. 2008).

Takazoe M. et al., "Sargramostim in Patients With Crohn's Disease: Results of a Phase 1-2 Study", J Gastroenterol 44:535-543 (2009).

Goetz M. et al., "Exacerbation of Ulcerative Colitis After Rituximab Salvage Therapy", Inflamm Bowel Dis 13 (11):1365-1368 (Nov. 2007).

International Search Report dated Feb. 15, 2013 received from the Australian Patent Office from related Application No. PCT/AU2012/001547.

Dieckgraefe B K et al., "Treatment of Active Crohn's Disease With Recombinant Human Granulocyte-Macrophage Colony-Stimulating Factor", The Lancet 360:1478-1480 (Nov. 9, 2002).

Rini B. et al., "Kinetics of Development and Characteristics of Antibodies Induced in Cancer Patients Against Yeast Expressed rDNA Derived Granulocyte Macrophage Colony Stimulating Factor (GM-CSF)", Cytokine 29:56-66 (2005).

* cited by examiner

*Primary Examiner* — Gyan Chandra

(74) *Attorney, Agent, or Firm* — Scully, Scott, Murphy & Presser, P.C.

(57) ABSTRACT

A method for treating or preventing an inflammatory bowel disease (IBD) in a subject, the method comprising administering to the subject a compound that inhibits granulocyte-macrophage colony stimulating factor (GM-CSF) signaling.

10 Claims, 1 Drawing Sheet

SEQUENCE LISTING

<160> NUMBER OF SEQ ID NOS: 6

<210> SEQ ID NO 1

```
<211> LENGTH: 435
<212> TYPE: DNA
<213> ORGANISM: homo sapiens

<400> SEQUENCE: 1

atgtggctgc agagcctgct gctcttgggc actgtggcct gcagcatctc tgcacccgcc     60

cgctcgccca gccccagcac gcagccctgg gagcatgtga atgccatcca ggaggcccgg    120

cgtctcctga acctgagtag agacactgct gctgagatga atgaaacagt agaagtcatc    180

tcagaaatgt ttgacctcca ggagccgacc tgcctacaga cccgcctgga gctgtacaag    240

cagggcctgc ggggcagcct caccaagctc aagggcccct tgaccatgat ggccagccac    300

tacaagcagc actgccctcc aaccccggaa acttcctgtg caacccagat tatcaccttt    360

gaaagtttca aagagaacct gaaggacttt ctgcttgtca tcccctttga ctgctgggag    420

ccagtccagg agtga                                                     435


<210> SEQ ID NO 2
<211> LENGTH: 127
<212> TYPE: PRT
<213> ORGANISM: homo sapiens

<400> SEQUENCE: 2

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125


<210> SEQ ID NO 3
<211> LENGTH: 1203
<212> TYPE: DNA
<213> ORGANISM: Homo sapiens

<400> SEQUENCE: 3

atgcttctcc tggtgacaag ccttctgctc tgtgagttac cacacccagc attcctcctg     60

atcccagaga aatcggatct gcgaacagtg gcaccagcct ctagtctcaa tgtgaggttt    120

gactccagga cgatgaattt aagctgggac tgccaagaaa acacaacctt cagcaagtgt    180

ttcttaactg acaagaagaa cagagtcgtg gaacccaggc tcagtaacaa cgaatgttcg    240

tgcacatttc gtgaaatttg tctgcatgaa ggagtcacat ttgaggttca cgtgaatact    300

agtcaaagag gatttcaaca gaaactgctt tatccaaatt caggaaggga gggtaccgct    360

gctcagaatt tctcctgttt catctacaat gcggatttaa tgaactgtac ctgggcgagg    420

ggtccgacgg ccccccgtga cgtccagtat tttttgtaca tacgaaactc aaagagaagg    480

agggagatcc ggtgtcctta ttacatacaa gactcaggaa cccatgtggg atgtcacctg    540
```

```
gataacctgt caggattaac gtctcgcaat tactttctgg ttaacggaac cagccgagaa    600

attggcatcc aattctttga ttcacttttg gacacaaaga aaatagaacg attcaaccct    660

cccagcaatg tcaccgtacg ttgcaacacg acgcactgcc tcgtacggtg gaaacagccc    720

aggacctatc agaagctgtc gtacctggac tttcagtacc agctggacgt ccacagaaag    780

aatacccagc ctggcacgga aaacctactg attaatgttt ctggtgattt ggaaaataga    840

tacaactttc caagctctga gcccagagca aaacacagtg tgaagatcag agctgcagac    900

gtccgcatct tgaattggag ctcctggagt gaagccattg aatttggttc tgacgacggg    960

aacctcggct ctgtgtacat ttatgtgctc ctaatcgtgg gaacccttgt ctgtggcatc   1020

gtcctcggct tcctctttaa aaggttcctt aggatacagc ggctgttccc gccagttcca   1080

cagatcaaag acaaactgaa tgataaccat gaggtggaag acgagatcat ctgggaggaa   1140

ttcaccccag aggaagggaa aggctaccgc gaagaggtct tgaccgtgaa ggaaattacc   1200

tga                                                                 1203


<210> SEQ ID NO 4
<211> LENGTH: 381
<212> TYPE: PRT
<213> ORGANISM: Homo sapiens

<400> SEQUENCE: 4

Leu Ile Pro Glu Lys Ser Asp Leu Arg Thr Val Ala Pro Ala Ser Ser
1               5                   10                  15

Leu Asn Val Arg Phe Asp Ser Arg Thr Met Asn Leu Ser Trp Asp Cys
            20                  25                  30

Gln Glu Asn Thr Thr Phe Ser Lys Cys Phe Leu Thr Asp Lys Lys Asn
        35                  40                  45

Arg Val Val Glu Pro Arg Leu Ser Asn Asn Glu Cys Ser Cys Thr Phe
    50                  55                  60

Arg Glu Ile Cys Leu His Glu Gly Val Thr Phe Glu Val His Val Asn
65                  70                  75                  80

Thr Ser Gln Arg Gly Phe Gln Gln Lys Leu Leu Tyr Pro Asn Ser Gly
                85                  90                  95

Arg Glu Gly Thr Ala Ala Gln Asn Phe Ser Cys Phe Ile Tyr Asn Ala
            100                 105                 110

Asp Leu Met Asn Cys Thr Trp Ala Arg Gly Pro Thr Ala Pro Arg Asp
        115                 120                 125

Val Gln Tyr Phe Leu Tyr Ile Arg Asn Ser Lys Arg Arg Arg Glu Ile
    130                 135                 140

Arg Cys Pro Tyr Tyr Ile Gln Asp Ser Gly Thr His Val Gly Cys His
145                 150                 155                 160

Leu Asp Asn Leu Ser Gly Leu Thr Ser Arg Asn Tyr Phe Leu Val Asn
                165                 170                 175

Gly Thr Ser Arg Glu Ile Gly Ile Gln Phe Phe Asp Ser Leu Leu Asp
            180                 185                 190

Thr Lys Lys Ile Glu Arg Phe Asn Pro Pro Ser Asn Val Thr Val Arg
        195                 200                 205

Cys Asn Thr Thr His Cys Leu Val Arg Trp Lys Gln Pro Arg Thr Tyr
    210                 215                 220

Gln Lys Leu Ser Tyr Leu Asp Phe Gln Tyr Gln Leu Asp Val His Arg
225                 230                 235                 240

Lys Asn Thr Gln Pro Gly Thr Glu Asn Leu Leu Ile Asn Val Ser Gly
```

```
                245                 250                 255

Asp Leu Glu Asn Arg Tyr Asn Phe Pro Ser Ser Glu Pro Arg Ala Lys
            260                 265                 270

His Ser Val Lys Ile Arg Ala Ala Asp Val Arg Ile Leu Asn Trp Ser
        275                 280                 285

Ser Trp Ser Glu Ala Ile Glu Phe Gly Ser Asp Asp Gly Asn Leu Gly
    290                 295                 300

Ser Val Tyr Ile Tyr Val Leu Leu Ile Val Gly Thr Leu Val Cys Gly
305                 310                 315                 320

Ile Val Leu Gly Phe Leu Phe Lys Arg Phe Leu Arg Ile Gln Arg Leu
                325                 330                 335

Phe Pro Pro Val Pro Gln Ile Lys Asp Lys Leu Asn Asp Asn His Glu
            340                 345                 350

Val Glu Asp Glu Ile Ile Trp Glu Glu Phe Thr Pro Glu Glu Gly Lys
        355                 360                 365

Gly Tyr Arg Glu Glu Val Leu Thr Val Lys Glu Ile Thr
    370                 375                 380


<210> SEQ ID NO 5
<211> LENGTH: 2694
<212> TYPE: DNA
<213> ORGANISM: Homo sapiens

<400> SEQUENCE: 5

atggtgctgg cccaggggct gctctccatg gccctgctgg ccctgtgctg ggagcgcagc      60

ctggcagggg cagaagaaac catcccgctg cagaccctgc gctgctacaa cgactacacc     120

agccacatca cctgcaggtg ggcagacacc caggatgccc agcggctcgt caacgtgacc     180

ctcattcgcc gggtgaatga ggacctcctg gagccagtgt cctgtgacct cagtgatgac     240

atgccctggt cagcctgccc ccatccccgc tgcgtgccca ggagatgtgt cattccctgc     300

cagagttttg tcgtcactga cgttgactac ttctcattcc aaccagacag gcctctgggc     360

acccggctca ccgtcactct gacccagcat gtccagcctc ctgagcccag ggacctgcag     420

atcagcaccg accaggacca cttcctgctg acctggagtg tggcccttgg gagtccccag     480

agccactggt tgtccccagg ggatctggag tttgaggtgg tctacaagcg gcttcaggac     540

tcttgggagg acgcagccat cctcctctcc aacacctccc aggccaccct ggggccagag     600

cacctcatgc ccagcagcac ctacgtggcc cgagtacgga cccgcctggc cccaggttct     660

cggctctcag gacgtcccag caagtggagc ccagaggttt gctgggactc ccagccaggg     720

gatgaggccc agccccagaa cctggagtgc ttctttgacg gggccgccgt gctcagctgc     780

tcctgggagg tgaggaagga ggtggccagc tcggtctcct ttggcctatt ctacaagccc     840

agcccagatg caggggagga agagtgctcc ccagtgctga gggaggggct cggcagcctc     900

cacaccaggc accactgcca gattcccgtg cccgaccccg cgacccacgg ccaatacatc     960

gtctctgttc agccaaggag ggcagagaaa cacataaaga gctcagtgaa catccagatg    1020

gcccctccat ccctcaacgt gaccaaggat ggagacagct acagcctgcg ctgggaaaca    1080

atgaaaatgc gatacgaaca catagaccac acatttgaga tccagtacag gaaagacacg    1140

gccacgtgga aggacagcaa gaccgagacc ctccagaacg cccacagcat ggccctgcca    1200

gccctggagc cctccaccag gtactgggcc agggtgaggg tcaggacctc ccgcaccggc    1260

tacaacggga tctggagcga gtggagtgag gcgcgctcct gggacaccga gtcggtgctg    1320

cctatgtggg tgctggccct catcgtgatc ttcctcacca tcgctgtgct cctggccctc    1380
```

cgcttctgtg gcatctacgg gtacaggctg cgcagaaagt gggaggagaa gatccccaac 1440
cccagcaaga gccacctgtt ccagaacggg agcgcagagc tttggccccc aggcagcatg 1500
tcggccttca ctagcgggag tcccccacac caggggccgt ggggcagccg cttccctgag 1560
ctggaggggg tgttccctgt aggattcggg gacagcgagg tgtcacctct caccatagag 1620
gaccccaagc atgtctgtga tccaccatct gggcctgaca cgactccagc tgcctcagat 1680
ctacccacag agcagccccc cagcccccag ccaggcccgc ctgccgcctc ccacacacct 1740
gagaaacagg cttccagctt tgacttcaat gggccctacc tggggccgcc ccacagccgc 1800
tccctacctg acatcctggg ccagccggag cccccacagg agggtgggag ccagaagtcc 1860
ccacctccag ggtccctgga gtacctgtgt ctgcctgctg gggggcaggt gcaactggtc 1920
cctctggccc aggcgatggg accaggacag gccgtggaag tggagagaag gccgagccag 1980
ggggctgcag ggagtccctc cctggagtcc gggggaggcc ctgcccctcc tgctcttggg 2040
ccaagggtgg gaggacagga ccaaaaggac agccctgtgg ctatacccat gagctctggg 2100
gacactgagg accctggagt ggcctctggt tatgtctcct ctgcagacct ggtattcacc 2160
ccaaactcag gggcctcgtc tgtctcccta gttccctctc tgggcctccc ctcagaccag 2220
acccccagct tatgtcctgg gctggccagt ggacccccctg gagccccagg ccctgtgaag 2280
tcagggtttg agggctatgt ggagctccct ccaattgagg gccggtcccc caggtcacca 2340
aggaacaatc ctgtcccccc tgaggccaaa agccctgtcc tgaacccagg ggaacgcccg 2400
gcagatgtgt ccccaacatc cccacagccc gagggcctcc ttgtcctgca gcaagtgggc 2460
gactattgct tcctccccgg cctgggggccc ggccctctct cgctccggag taaaccttct 2520
tccccgggac ccggtcctga gatcaagaac ctagaccagg cttttcaagt caagaagccc 2580
ccaggccagg ctgtgcccca ggtgcccgtc attcagctct tcaaagccct gaagcagcag 2640
gactacctgt ctctgccccc ttgggaggtc aacaagcctg ggaggtgtg ttga 2694

<210> SEQ ID NO 6
<211> LENGTH: 881
<212> TYPE: PRT
<213> ORGANISM: Homo sapiens

<400> SEQUENCE: 6

Trp Glu Arg Ser Leu Ala Gly Ala Glu Glu Thr Ile Pro Leu Gln Thr
1 5 10 15

Leu Arg Cys Tyr Asn Asp Tyr Thr Ser His Ile Thr Cys Arg Trp Ala
20 25 30

Asp Thr Gln Asp Ala Gln Arg Leu Val Asn Val Thr Leu Ile Arg Arg
35 40 45

Val Asn Glu Asp Leu Leu Glu Pro Val Ser Cys Asp Leu Ser Asp Asp
50 55 60

Met Pro Trp Ser Ala Cys Pro His Pro Arg Cys Val Pro Arg Arg Cys
65 70 75 80

Val Ile Pro Cys Gln Ser Phe Val Val Thr Asp Val Asp Tyr Phe Ser
85 90 95

Phe Gln Pro Asp Arg Pro Leu Gly Thr Arg Leu Thr Val Thr Leu Thr
100 105 110

Gln His Val Gln Pro Pro Glu Pro Arg Asp Leu Gln Ile Ser Thr Asp
115 120 125

Gln Asp His Phe Leu Leu Thr Trp Ser Val Ala Leu Gly Ser Pro Gln
130 135 140

-continued

```
Ser His Trp Leu Ser Pro Gly Asp Leu Glu Phe Glu Val Val Tyr Lys
145                 150                 155                 160

Arg Leu Gln Asp Ser Trp Glu Asp Ala Ala Ile Leu Leu Ser Asn Thr
                165                 170                 175

Ser Gln Ala Thr Leu Gly Pro Glu His Leu Met Pro Ser Ser Thr Tyr
            180                 185                 190

Val Ala Arg Val Arg Thr Arg Leu Ala Pro Gly Ser Arg Leu Ser Gly
        195                 200                 205

Arg Pro Ser Lys Trp Ser Pro Glu Val Cys Trp Asp Ser Gln Pro Gly
    210                 215                 220

Asp Glu Ala Gln Pro Gln Asn Leu Glu Cys Phe Phe Asp Gly Ala Ala
225                 230                 235                 240

Val Leu Ser Cys Ser Trp Glu Val Arg Lys Glu Val Ala Ser Ser Val
                245                 250                 255

Ser Phe Gly Leu Phe Tyr Lys Pro Ser Pro Asp Ala Gly Glu Glu Glu
            260                 265                 270

Cys Ser Pro Val Leu Arg Glu Gly Leu Gly Ser Leu His Thr Arg His
        275                 280                 285

His Cys Gln Ile Pro Val Pro Asp Pro Ala Thr His Gly Gln Tyr Ile
    290                 295                 300

Val Ser Val Gln Pro Arg Arg Ala Glu Lys His Ile Lys Ser Ser Val
305                 310                 315                 320

Asn Ile Gln Met Ala Pro Pro Ser Leu Asn Val Thr Lys Asp Gly Asp
                325                 330                 335

Ser Tyr Ser Leu Arg Trp Glu Thr Met Lys Met Arg Tyr Glu His Ile
            340                 345                 350

Asp His Thr Phe Glu Ile Gln Tyr Arg Lys Asp Thr Ala Thr Trp Lys
        355                 360                 365

Asp Ser Lys Thr Glu Thr Leu Gln Asn Ala His Ser Met Ala Leu Pro
    370                 375                 380

Ala Leu Glu Pro Ser Thr Arg Tyr Trp Ala Arg Val Arg Val Arg Thr
385                 390                 395                 400

Ser Arg Thr Gly Tyr Asn Gly Ile Trp Ser Glu Trp Ser Glu Ala Arg
                405                 410                 415

Ser Trp Asp Thr Glu Ser Val Leu Pro Met Trp Val Leu Ala Leu Ile
            420                 425                 430

Val Ile Phe Leu Thr Ile Ala Val Leu Leu Ala Leu Arg Phe Cys Gly
        435                 440                 445

Ile Tyr Gly Tyr Arg Leu Arg Arg Lys Trp Glu Glu Lys Ile Pro Asn
    450                 455                 460

Pro Ser Lys Ser His Leu Phe Gln Asn Gly Ser Ala Glu Leu Trp Pro
465                 470                 475                 480

Pro Gly Ser Met Ser Ala Phe Thr Ser Gly Ser Pro Pro His Gln Gly
                485                 490                 495

Pro Trp Gly Ser Arg Phe Pro Glu Leu Glu Gly Val Phe Pro Val Gly
            500                 505                 510

Phe Gly Asp Ser Glu Val Ser Pro Leu Thr Ile Glu Asp Pro Lys His
        515                 520                 525

Val Cys Asp Pro Pro Ser Gly Pro Asp Thr Thr Pro Ala Ala Ser Asp
    530                 535                 540

Leu Pro Thr Glu Gln Pro Pro Ser Pro Gln Pro Gly Pro Pro Ala Ala
545                 550                 555                 560
```

-continued

```
Ser His Thr Pro Glu Lys Gln Ala Ser Ser Phe Asp Phe Asn Gly Pro
                565                 570                 575

Tyr Leu Gly Pro Pro His Ser Arg Ser Leu Pro Asp Ile Leu Gly Gln
            580                 585                 590

Pro Glu Pro Pro Gln Glu Gly Gly Ser Gln Lys Ser Pro Pro Pro Gly
        595                 600                 605

Ser Leu Glu Tyr Leu Cys Leu Pro Ala Gly Gly Gln Val Gln Leu Val
    610                 615                 620

Pro Leu Ala Gln Ala Met Gly Pro Gly Gln Ala Val Glu Val Glu Arg
625                 630                 635                 640

Arg Pro Ser Gln Gly Ala Ala Gly Ser Pro Ser Leu Glu Ser Gly Gly
                645                 650                 655

Gly Pro Ala Pro Pro Ala Leu Gly Pro Arg Val Gly Gly Gln Asp Gln
            660                 665                 670

Lys Asp Ser Pro Val Ala Ile Pro Met Ser Ser Gly Asp Thr Glu Asp
        675                 680                 685

Pro Gly Val Ala Ser Gly Tyr Val Ser Ser Ala Asp Leu Val Phe Thr
    690                 695                 700

Pro Asn Ser Gly Ala Ser Ser Val Ser Leu Val Pro Ser Leu Gly Leu
705                 710                 715                 720

Pro Ser Asp Gln Thr Pro Ser Leu Cys Pro Gly Leu Ala Ser Gly Pro
                725                 730                 735

Pro Gly Ala Pro Gly Pro Val Lys Ser Gly Phe Glu Gly Tyr Val Glu
            740                 745                 750

Leu Pro Pro Ile Glu Gly Arg Ser Pro Arg Ser Pro Arg Asn Asn Pro
        755                 760                 765

Val Pro Pro Glu Ala Lys Ser Pro Val Leu Asn Pro Gly Glu Arg Pro
    770                 775                 780

Ala Asp Val Ser Pro Thr Ser Pro Gln Pro Glu Gly Leu Leu Val Leu
785                 790                 795                 800

Gln Gln Val Gly Asp Tyr Cys Phe Leu Pro Gly Leu Gly Pro Gly Pro
                805                 810                 815

Leu Ser Leu Arg Ser Lys Pro Ser Ser Pro Gly Pro Gly Pro Glu Ile
            820                 825                 830

Lys Asn Leu Asp Gln Ala Phe Gln Val Lys Lys Pro Pro Gly Gln Ala
        835                 840                 845

Val Pro Gln Val Pro Val Ile Gln Leu Phe Lys Ala Leu Lys Gln Gln
    850                 855                 860

Asp Tyr Leu Ser Leu Pro Pro Trp Glu Val Asn Lys Pro Gly Glu Val
865                 870                 875                 880

Cys
```

METHOD OF TREATING INFLAMMATORY BOWEL DISEASE

RELATED APPLICATION DATA

The present application claims priority from U.S. Patent Application No. 61/579,555, entitled "Method of treating inflammatory bowel disease", filed 22 Dec. 2011. The entire contents of that application is hereby incorporated by reference.

FIELD

The present disclosure relates to method for treating inflammatory bowel disease.

BACKGROUND

Inflammatory bowel disease (IBD) is a disorder of unknown etiology characterized typically by diarrhea, cramping, abdominal pains, weight loss and rectal bleeding, tiredness, anemia, fistulae, perforations, obstruction of the bowel and frequent need for surgical intervention. According to the US Center for Disease Control and Prevention, about 1.4 million people in USA suffer from IBD, making it one of the most prevalent gastrointestinal diseases in the United States. The overall healthcare cost of IBD in USA is estimated to be more than US$1.7 billion per year.

A number of disorders fall within the class of IBD, including Crohn's disease, ulcerative colitis, indeterminate colitis, microscopic colitis and collagenous colitis. The most common forms of IBD are Crohn's disease and ulcerative colitis. Ulcerative colitis affects the large intestine (colon) and rectum and involves the inner lining (e.g., the mucosal and submucosal layer) of the intestinal wall. Crohn's disease may affect any section of the gastrointestinal tract (e.g., mouth, esophagus, stomach, small intestine, large intestine, rectum, anus, etc.) and may involve all layers of the intestinal wall. The clinical symptoms of IBD include rectal and/or intestinal bleeding, abdominal pain and cramping, diarrhea, and weight loss. In addition, IBD is a risk factor for colon cancer, and this risk for colon cancer increases significantly after eight to ten years of IBD.

IBD has no cure. Current therapies for IBD are directed at reducing the inflammatory process and at reducing the detrimental effects of the inflammatory process associated with the disease, and include administration of anti-inflammatory drugs (e.g., mesalamine, sulfasalazine, infliximab, adalimumab, prednisone, budesonide) and of immunosuppressive drugs (e.g., 6-mercaptopurine, azathioprine, cyclosporine). Such therapies are often associated with adverse side effects, such as nausea, vomiting, anorexia, dyspepsia, malaise, headaches, abdominal pain, fever, rash, pancreatitis, bone marrow suppression, formation of antibodies, infusion reactions, and increased opportunistic infections.

It is clear from the foregoing that treatments for IBD are required.

Certain patent applications speculate that antibodies that neutralize granulocyte-macrophage colony stimulating factor (GM-CSF) signaling may be a potential treatment for a variety of autoimmune conditions, including arthritis, multiple sclerosis, lung inflammation, atherosclerosis and IBD. Despite this speculation, research conducted in the field of treating IBD suggests that GM-CSF itself may be a therapeutic agent for this disorder. For example, Sainathan et al., (*Inflamm Bowel Dis.* 14: 88-99, 2008) showed that GM-CSF significantly improved clinical parameters in a model of colitis. Studies in humans have also shown that Sargramostim (GM-CSF) provides a benefit in some patients suffering from Crohn's disease (e.g., Korzenik et al., *N Engl J Med.* 352: 2193-201, 2005; Takazoe et al., *J Gastroenterol.* 44: 535-43, 2009; Valentine et al., *Gut.* 58:1354-62, 2009; and Kelsen et al., *Inflamm Bowel Dis.* 16:1203-8, 2010). For example, Korzenik et al., showed a significant increase in the number of patients receiving treatment with Sargramostim who achieved a reduction of Crohn's Disease Activity Index (CDAI) of 100 points or entered remission compared to placebo. These results are consistent with the findings of Goldstein et al., (*Gastroenterology* 141: 208-216, 2011) who showed that decreased levels and activity of GM-CSFR is associated with IBD in humans. These findings indicate that IBD is different to several other autoimmune disorders, in which administering GM-CSF actually exacerbates the symptoms of the disorder, e.g., arthritis, multiple sclerosis, lung inflammation or atheroscelerosis.

SUMMARY

In producing the present invention, the inventors proceeded against current evidence-based opinion in the art that IBD is treated by increasing GM-CSF in a subject. Instead, the inventors inhibited GM-CSF signaling in a subject. Rather than exacerbating MD as would be expected based on the discussion herein-above, the inventors found that they reduced the symptoms of IBD. Thus, the present inventors have produced a method of treating IBD.

In one example, the present disclosure provides a method for treating or preventing an inflammatory bowel disease (IBD) in a subject, the method comprising administering to the subject a compound that inhibits GM-CSF signaling.

For example, the IBD is characterized by inflammation in the digestive system. In one example, the inflammation is in the intestine, e.g., within the mucosa of the intestine. In one example, the inflammation is within the large or small intestine or within the colon.

For example, the IBD is characterized by an innate immune response in the digestive system. In one example, the innate immune response is in the intestine, e.g., within the mucosa of the intestine. In one example, the innate immune response is within the large or small intestine or within the colon.

In one example, the IBD is characterized by an innate immune response in the digestive system and an adaptive immune response in the digestive system.

In one example, the IBD is characterized by a systemic innate immune response.

In one example, the IBD is characterized by a systemic innate immune response and a systemic adaptive immune response.

In one example, the IBD is characterized by a CD40-mediated immune response.

In one example, the method comprises identifying a subject suffering from the immune response discussed above.

In one example, the IBD is ulcerative colitis or Crohn's disease. In one example, the IBD is Crohn's disease.

In one example, the compound is administered in an amount sufficient to inhibit or prevent an innate immune response in the digestive system and/or a systemic innate immune response.

In one example, the present disclosure provides a method for inhibiting or preventing an innate immune response (e.g., an innate immune response in the digestive system and/or a systemic innate immune response) in a subject suffering from an IBD, the method comprising administering a compound that inhibits GM-CSF signaling in the subject. Exemplary IBDs are discussed above and are to be taken to apply to this example of the disclosure.

In one example, the present disclosure provides a method for inhibiting or preventing weight loss in a subject suffering from an IBD, the method comprising administering a compound that inhibits GM-CSF signaling in the subject. Exemplary IBDs are discussed above and are to be taken to apply to this example of the disclosure.

In one example, a compound that inhibits GM-CSF signaling binds to GM-CSF or GM-CSFR. For example, the compound is selected from the group consisting of:

(i) a protein comprising an antibody variable region that binds to or specifically binds to GM-CSF or GM-CSFR and neutralizes GM-CSF-signaling;

(ii) a soluble GM-CSF receptor (GM-CSFR) or GM-CSF binding region thereof.

In one example, the compound is a GM-CSF-binding protein comprising an antibody variable region that specifically binds to GM-CSF and neutralizes GM-CSF-signaling.

An exemplary compound is a GM-CSFR-binding protein comprising an antibody variable region that binds to or specifically binds to GM-CSFR and neutralizes GM-CSF-signaling.

In one example, a compound is a domain antibody (e.g., comprising only a heavy chain variable region or only a light chain variable region that binds to GM-CSF or GM-CSFR) or a heavy chain only antibody (e.g., a camelid antibody or an IgNAR) or variable region thereof.

In one example, a compound is a protein comprising a Fv. For example, the protein is selected from the group consisting of:

(i) a single chain Fv fragment (scFv);

(ii) a dimeric scFv (di-scFv); or (iv) a diabody;

(v) a triabody;

(vi) a tetrabody;

(vii) a Fab;

(viii) a $F(ab')_2$;

(ix) a Fv; or (x) one of (i) to (ix) linked to a constant region of an antibody, Fc or a heavy chain constant domain $(C_H)$ 2 and/or $C_H3$.

In another example, a compound is an antibody. Exemplary antibodies are full-length and/or naked antibodies.

In one example, the compound is a protein that is recombinant, chimeric, CDR grafted, humanized, synhumanized, primatized, deimmunized or human.

In one example, the compound that inhibits GM-CSF signaling inhibits or prevents expression of GM-CSF and/or GM-CSFR. For example, the compound is selected from the group an antisense, a siRNA, a RNAi, a ribozyme and a DNAzyme.

In one example, a method described herein for preventing an IBD comprises administering the compound to a subject who suffers from the IBD while they are in remission to thereby prevent relapse of the IBD.

Methods of treatment described herein can additionally comprise administering a further compound to treat or prevent the IBD.

The present disclosure also provides a compound that inhibits GM-CSF signaling for use in the treatment or prevention of an IBD.

The present disclosure also provides for use of a compound that inhibits GM-CSF signaling in the manufacture of a medicament for treating or preventing an IBD.

The present disclosure also provides a kit comprising a compound that inhibits GM-CSF signaling packaged with instructions for use in the treatment of an inflammatory bowel disease.

Exemplary IBDs and compounds are described herein and are to be taken to apply mutatis mutandis to the examples of the disclosure set out in the previous three paragraphs.

KEY TO SEQUENCE LISTING

Figure 1A:
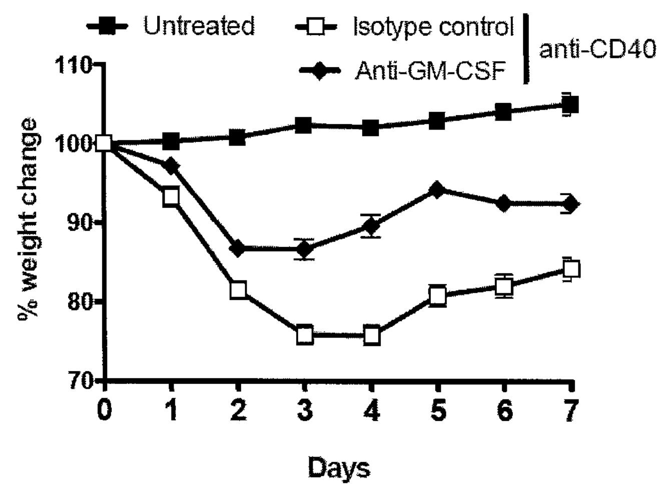
FIG. 1A is a graphical representation showing treatment of an animal model of IBD with anti-GM-CSF antibody inhibits weight loss. As shown the percentage weight change from pretreatment weight was less for animals treated with anti-GM-CSF antibody than isotype control antibody (as labeled). The line labeled "Untreated" depicts results for animals in which IBD was not induced and that did not receive any antibody treatment.

SEQ ID NO: 1 is an amino acid sequence of a human GM-CSF

SEQ ID NO: 2 is a nucleotide sequence encoding a human GM-CSF.

SEQ ED NO: 3 is an amino acid sequence of a GM-CSFR α subunit or α chain.

SEQ ID NO: 4 is a nucleotide sequence encoding a GM-CSFR α subunit or α chain.

SEQ ID NO: 5 is an amino acid sequence of a GM-CSFR βc subunit or βc chain.

SEQ ID NO: 6 is a nucleotide sequence encoding a GM-CSFR βc subunit or βc chain.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Any example of the present disclosure in relation to treatment or prevention of an IBD shall be taken to apply mutatis mutandis to inhibiting or preventing an innate immune response (e.g., an innate immune response in the digestive system and/or a systemic innate immune response) in a subject suffering from an IBD.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

For the purposes of nomenclature only and not limitation an exemplary sequence of a human GM-CSF is set out in NCBI Reference Sequence: NP_000749.2 (and set out in SEQ ID NO: 2). A sequence encoding this protein is set forth in SEQ ID NO: 1.

The skilled artisan will be aware that "GM-CSFR" is a heterodimeric protein comprising an α subunit (syn. CD116), which specifically binds to GM-CSF, and a βc subunit (syn. CD131), which is involved in high affinity binding and signal transduction and is shared with the receptors for interleukins-3 and -5. For the purposes of nomenclature only and not limitation an exemplary sequence of a human GM-CSFR α subunit is set out in NCBI Reference Sequence: NP_006131 (and set out in SEQ ID NO: 4). A sequence encoding this protein is set forth in SEQ ID NO: 3. For the purposes of nomenclature only and not limitation an exemplary sequence of a human GM-CSFR βc subunit is set out in NCBI Reference Sequence: NP_000386.1 (and set out in SEQ ID NO: 6). A sequence encoding this protein is set forth in SEQ ID NO: 3. Additional sequence of GM-CSFR subunits can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)) Reference to human GM-CSFR may be abbreviated to hGM-CSFR.

The term "inflammatory bowel disease" or "IBD" refers to a group of disorders that cause the intestines to become inflamed, generally manifested with symptoms including abdominal cramps and pain, diarrhea, weight loss and intestinal bleeding. The main forms of IBD are ulcerative colitis (UC) and Crohn's disease.

"Ulcerative colitis" or "UC" is a chronic, episodic, inflammatory disease of the large intestine and rectum characterized by bloody diarrhea. Ulcerative colitis is characterized by chronic inflammation in the colonic mucosa and can be categorized according to location: "proctitis" involves only the rectum, "proctosigmoiditis" affects the rectum and sigmoid colon, "left-sided colitis" encompasses the entire left side of the large intestine, "pancolitis" inflames the entire colon.

"Crohn's disease," also called "regional enteritis," is a chronic autoimmune disease that can affect any part of the gastrointestinal tract but most commonly occurs in the ileum (the area where the small and large intestine meet). Crohn's disease, in contrast to ulcerative colitis, is characterized by chronic inflammation extending through all layers of the intestinal wall and involving the mesentery as well as regional lymph nodes. Whether or not the small bowel or colon is involved, the basic pathologic process is the same.

Ulcerative Colitis and Crohn's disease can be distinguished from each other clinically, endoscopically, pathologically, and serologically in more than 90% of cases; the remainder are considered to be indeterminate IBD (Harrison's Principles of Internal medicine, 12th edition, p. 1271 (1991)).

The term "adaptive immune response" will be understood by the skilled artisan to include an immune response involving or induced by T lymphocytes, such as $CD8^+$ T lymphocytes and/or helper T-cells or B cells.

The term "innate immune response" will be understood by the skilled person to be effected by cells and mechanisms that defend the host from infection by other organisms in a non-specific manner, i.e., the cells of the innate system recognize and respond to pathogens in a generic way, but unlike the adaptive immune system, it does not confer long-lasting or protective immunity to the host. Cells of the innate immune response include phagocytes, such as macrophages, neutrophils, dendritic cells, basophils and eosinophils, natural killer cells and γδ T cells. The complement system also forms a component of the innate immune system. An innate immune response can induce an adaptive immune response.

By "CD40-mediated immune response" is meant an immune response that is induced or maintained by interaction of C40 on antigen presenting cells with CD40 ligand (CD40L; C154) on $T_H$ cells. A CD40-mediated immune response can be detected by identifying CD40 and/or CD40L expressing cells in a sample from a subject, e.g., by immunofluorescence, immunohistochemistry and/or fluorescence activated cell sorting. A CD40-mediated immune response can also be detected by detecting increased levels of proteins produced by cells involved in such an immune response, e.g., interleukin-6, interleukin-8, interleukin-1βtumor necrosis factor-α or monocyte chemotactic protein-1.

The term "recombinant" shall be understood to mean the product of artificial genetic recombination. Accordingly, in the context of a recombinant protein comprising an antibody variable region, this term does not encompass an antibody naturally-occurring within a subject's body that is the product of natural recombination that occurs during B cell maturation. However, if such an antibody is isolated, it is to be considered an isolated protein comprising an antibody variable region. Similarly, if nucleic acid encoding the protein is isolated and expressed using recombinant means, the resulting protein is a recombinant protein comprising an antibody variable region. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The skilled artisan will be aware that an "antibody" is generally considered to be a protein that comprises a variable region made up of a plurality of polypeptide chains, e.g., a polypeptide comprising a light chain variable region ($V_L$) and a polypeptide comprising a heavy chain variable region ($V_H$). An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ϵ, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies, synhumanized antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. The amino acid positions assigned to CDRs and FRs can be defined according to Kabat *Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196: 901-917, 1987; Chothia et al. *Nature* 342, 877-883, 1989; and/or Al-Lazikani et al., *J Mol Biol* 273: 927-948, 1997; the IMGT numbering system of Lefranc et al., *Devel. And Compar. Immunol.*, 27: 55-77, 2003; or the AHO numbering system of Honnegher and Plükthun *J. Mol. Biol.*, 309: 657-670, 2001.

"Framework regions" (FRs) are those variable domain residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an antibody, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "$Fab_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker As used herein, the term "binds" in reference to the interaction of a protein or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a protein of the disclosure reacts or associates more frequently, more rapidly, with greater duration and/or with greater affinity with a particular antigen or cell expressing same than it does with alternative antigens or cells. For example, a protein binds to GM-CSFR with materially greater affinity (e.g., 20 fold or 40 fold or 60 fold or 80 fold to 100 fold or 150 fold or 200 fold) than it does to other cytokine receptor or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

The term "soluble granulocyte macrophage-colony stimulating factor receptor" (sGM-CSFR) refers to a non-membrane bound receptor that binds GM-CSF, but does not transduce a signal when bound to GM-CSF. In one example, the sGM-CSFR is a soluble form of GM-CSFRα chain, e.g., comprising a GM-CSF binding region of the receptor (e.g., an extracellular region of the receptor). In another example, the sGM-CSFR comprises a GM-CSF binding region of GM-CSFRα chain (e.g., an extracellular region of the GM-CSFRα chain) and a GM-CSF binding region of GM-CSFRβc chain chain (e.g., an extracellular region of the GM-CSFRβc chain).

As used herein, the term "neutralize" shall be taken to mean that a protein is capable of blocking, reducing or preventing GM-CSF-signaling in a cell through the GM-CSFR. Methods for determining neutralization are known in the art and/or described herein.

As used herein, the terms "preventing", "prevent" or "prevention" include administering a protein of the disclosure to thereby stop or hinder the development of at least one symptom of a condition. This term also encompasses treatment of a subject in remission to prevent or hinder relapse. For example, a subject suffering from relapsing-remitting IBD is treated during remission to thereby prevent a relapse.

As used herein, the terms "treating", "treat" or "treatment" include administering a protein described herein to thereby reduce or eliminate at least one symptom of a specified disease or condition.

As used herein, the term "subject" shall be taken to mean any animal including humans, for example a mammal. Exemplary subjects include but are not limited to humans and non-human primates. For example, the subject is a human.

Treatment of IBD

The disclosure herein provides, for example, a method for treating or preventing IBD in a subject comprising administering to the subject a compound that inhibits GM-CSF signaling.

In one example, the disclosure provides a method for treating a subject suffering from an active IBD. A subject with "active" IBD is experiencing at least one symptom of IBD at the time of screening or treatment (e.g., initial treatment).

A "symptom" of IBD is a morbid phenomenon or departure from the normal in structure, function, or sensation, experienced by the subject and indicative of IBD.

In one example, the IBD is characterized by an innate immune response in the digestive system. In one example, the innate immune response is in the intestine, e.g., within the mucosa of the intestine. In one example, the innate immune response is within the large or small intestine or within the colon.

Methods for detecting an innate immune response will be apparent to the skilled artisan. For example, a sample is obtained from a subject and cell(s) of the innate immune system are detected, e.g., by immunohistochemistry, immunofluorescence or flow cytometry. Detection of an increased number of cells compared to in a healthy subject (or population thereof) indicates presence of an innate immune response.

In one example, the IBD is characterized by an innate immune response in the digestive system and an adaptive immune response in the digestive system.

In one example, the IBD is characterized by a systemic innate immune response.

In one example, the disclosure provides a method for treating moderate-severe IBD in a subject.

"Moderate-severe" IBD is IBD where the signs or symptoms of disease in the subject are greater than mild. Such subjects can be identified by a skilled gastroenterologist. The subject with moderate-severe IBD may have been treated with oral corticosteroids for UC within 2 years prior to screening, and/or treatment intensity may have been equal to or greater than a prednisone equivalent dose of 20 mg/day for at least 2 weeks' duration. Such subjects may be steroid refractory and/or steroid-dependent. A subject with moderate-severe UC may be selected based on DAI score, for example, where a DAI score >6, >2 rectal bleeding score, and/or >2 flexible sigmoidoscopy score indicates the subject has moderate-severe UC. Alternatively, or additionally, the criteria for assessment of mild, moderate, and severe disease as in Truelove and Witts *Br Med J.* 2: 1041-1048, 1955) may be used to identify such subjects. Subjects with fulminant or toxic colitis usually have more than 10 bowel movements per day, continuous bleeding, abdominal distention and tenderness, and radiologic evidence of edema and possibly bowel dilation.

A "sigmoidoscopy" is an inspection, through an endoscope, of the interior of the sigmoid colon.

A "sigmoidoscopy score" refers to a score assigned by a clinician based on a sigmoidoscopy. An exemplary sigmoidscopy scoring system is as follows:

0=normal or inactive disease

1=mild disease (erythema, decreased vascular pattern, mild friability)

2=moderate disease (marked erythema, absent vascular pattern, friability, erosions)

3=severe disease (spontaneous bleeding, ulceration)

"Rectal bleeding" refers to any bleeding in or from the rectum.

A "rectal bleeding score" is the score or grade assigned for the extent, if any, of rectal bleeding. A daily bleeding score represents the most severe bleeding of the day. An exemplary rectal bleeding scoring system is:

0=no blood seen

1=streaks of blood with stool less than half the time

2=obvious blood with stool most of the time

3=blood alone passed.

A "disease activity index (DAI)" scoring system is a method for quantitatively assessing UC activity. An exemplary DAI scoring system is as follows:

DAI Scoring System for Assessment of UC Activity

Stool frequency (each subject serves as his/her own control to establish the degree of abnormality of the stool frequency)

0=normal number of stools for this subject

1=1-2 stools more than normal

2=3-4 stools more than normal

3=5 or more stools more than normal

Rectal bleeding (the daily bleeding score represented the most severe bleeding of the day)

0=no blood seen

1=streaks of blood with stool less than half the time

2=obvious blood with stool most of the time 3=blood alone passed.

Findings of flexible protosigmoidoscopy

0=normal or inactive disease

1=mild disease (erythema, decreased vascular pattern)

2=moderate disease (marked erythema, absent vascular pattern, friability, erosions)

3=severe disease (spontaneous bleeding, ulceration)

Physician's global assessment (acknowledges the 3 other criteria, the subject's daily record of abdominal discomfort and general sense of well-being, and other observations, such as physical findings and the subject' s performance status)

0=normal

1=mild disease

2=moderate disease

3=severe disease

In another example, a method of present disclosure treats a subject suffering from a steroid-refractory IBD. A "Steroid-refractory" IBD is IBD which progresses, or worsens, even though steroid is being administered to the subject with IBD. In a further example, a method of the present disclosure treat a subject with steroid dependent IBD. A subject with "steroid-dependent" IBD is dependent on steroid use, and can not taper or withdraw steroid administration due to persistent symptoms.

In one example, performing a method described herein according to any example of the disclosure results in a clinical response and/or disease remission.

By "clinical response" is meant an improvement in the symptoms of disease. The clinical response may be achieved within a certain time frame, for example, within or at about 8 weeks from the start of treatment with, or from the initial administration. Clinical response may also be sustained for a period of time, such as for >24 weeks, or ≥48 weeks. Clinical response may be evaluated in terms of a reduction in disease activity index (DAI) score, for example, the DAI score may be reduced by greater than or equal to 3 points.

In a further example, performing a method described herein according to any example may result in disease remission. In one example, the time to disease remission is less than that achieved in a subject who is not treated by performing a method described herein. In another example, the duration of remission is greater than that achieved in a subject who is not by a method described herein. For example, the duration of remission may be for at least 24 weeks, such as for at least 48 weeks.

By "disease remission" is intended substantially no evidence of the symptoms of disease. Remission may be achieved within a specified time frame, such as within or at about 8 weeks, from the start of treatment with, or from the initial dose of, the antagonist or antibody. Remission may also be sustained for a period of time, such as for ≥24 weeks, or ≥48 weeks. Disease remission may be defined as defined as a sigmoidoscopy score of 0 or 1 and/or rectal bleeding score of 0.

Subjects treated herein may:

be resistant or refractory to etanercept, infliximab, or adalimumab;

have been treated with a stable doses of aminosalicylate for >3 weeks;

have been treated with stable doses of oral corticosteroid dose for >2 weeks;

have been treated with 6-MP for a 3-month period, and with a stable dose thereof for >4 weeks;

have been treated with azathioprine for a 3-month period, with a stable dose for >4 weeks.

In one example, the remission is steroid-free remission.

Also provided by the present disclosure is a method for reducing a disease activity index (DAI) score in a subject suffering from an IBD the method comprising administering to the subject a compound that inhibits GM-CSF signaling to thereby reduce DAI score. In one example, administration of the compound reduces such DAI score by greater than or equal to 3 points.

GM-CSFR Signaling Inhibitors

Proteins Comprising Antibody Variable Regions

An exemplary GM-CSFR signaling inhibitor comprises an antibody variable region, e.g., is an antibody or an antibody fragment that binds to GM-CSF or GM-CSFR and neutralizes GM-CSF signaling.

In one example, the antibody variable region binds specifically to GM-CSFR.

In another example, the antibody variable region binds specifically to G-CSFR.

Suitable antibodies and proteins comprising variable regions thereof are known in the art. For example, anti-GM-CSFR antibodies and fragments thereof are described in WO2007/110631. An example of an anti-GM-CSFR antibody is mavrilimumab (CAM3001)

An example of an antibody specific for GM-CSFRβc chain is the BION-1 antibody which neutralizes GM-CSF (albeit a weak neutralizer of IL-5 and IL-3), the specifics of which are disclosed in WO1997028190.

Exemplary anti-GM-CSF antibodies are described, for example, in WO2007/049472 or WO2003/068920. Additional exemplary anti-GM-CSF antibodies include MORAb-022 (a human antibody; Morphotek), MOR103 (a human antibody; Morphosys), KB003 (a Humaneered® monoclonal antibody; Kalabios) and chimeric antibody 19.2 (a chimeric antibody; Kalobios). Exemplary disclosures of antibodies include WO2007/092939 (MORAb-022), WO2009/134805 (KB003), WO2006/122797 (MOR103) and US20080171038 (chimeric 19.2).

Additional anti-GM-CSF antibodies are described in WO2009/038760.

In another example, an antibody or protein comprising a variable region thereof is produced using a standard method.

Immunization-Based Methods

To generate antibodies, GM-CSF or GM-CSFR or an epitope bearing fragment or portion thereof or a modified form thereof or nucleic acid encoding same (an "immunogen"), optionally formulated with any suitable or desired adjuvant and/or pharmaceutically acceptable carrier, is administered to a subject (for example, a non-human animal subject, such as, a mouse, a rat, a chicken etc.) in the form of an injectable composition. Exemplary non-human animals are mammals, such as murine animals (e.g., rats or mice). Injection may be intranasal, intramuscular, sub-cutaneous, intravenous, intradermal, intraperitoneal, or by other known route. Optionally, the immunogen is administered numerous times. Means for preparing and characterizing antibodies are known in the art (See, e.g., Antibodies: A Laboratory Manual, Cold Spring Harbor Laboratory, 1988).

The production of polyclonal antibodies may be monitored by sampling blood of the immunized animal at various points following immunization. A second, booster injection, may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are exemplary antibodies contemplated by the present disclosure. Generally, production of monoclonal antibodies involves, immunizing a subject (e.g., a rodent, e.g., mouse or rat) with the immunogen under conditions sufficient to stimulate antibody producing cells. In some examples, a mouse genetically-engineered to express human antibodies and not express murine antibodies proteins, is immunized to produce an antibody (e.g., as described in PCT/US2007/008231 and/or Lonberg et al., *Nature* 368 (1994): 856-859). Following immunization, antibody producing somatic cells (e.g., B lymphocytes) are fused with immortal cells, e.g., immortal myeloma cells. Various methods for producing such fused cells (hybridomas) are known in the art and described, for example, in Kohler and Milstein, *Nature* 256, 495-497, 1975. The hybridoma cells can then be cultured under conditions sufficient for antibody production.

The present disclosure contemplates other methods for producing antibodies, e.g., ABL-MYC technology (as described, for example in Largaespada et al, *Curr. Top. Microbiol. Immunol,* 166, 91-96. 1990).

Library-Based Methods

The present disclosure also encompasses screening of libraries of antibodies or proteins comprising antigen binding domains thereof (e.g., comprising variable regions thereof) to identify a GM-CSF or GM-CSFR binding antibody or protein comprising a variable region thereof.

Examples of libraries contemplated by this disclosure include naïve libraries (from unchallenged subjects), immunized libraries (from subjects immunized with an antigen) or synthetic libraries. Nucleic acid encoding antibodies or regions thereof (e.g., variable regions) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001) and used to encode and display proteins using a method known in the art. Other techniques for producing libraries of proteins are described in, for example in U.S. Pat. No. 6,300,064 (e.g., a HuCAL library of Morphosys AG); U.S. Pat. Nos. 5,885,793; 6,204,023; 6,291,158; or 6,248,516.

The proteins according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding domains of antibodies are expressed on phage, e.g., as described in U.S. Pat. Nos. 6,300,064; 5,885,793; 6,204,023; 6,291,158; or 6,248,516. Other phage display methods are known in the art and are contemplated by the present disclosure. Similarly, methods of cell display are contemplated by the disclosure, e.g., bacterial display libraries, e.g., as described in U.S. Pat. No. 5,516,637; yeast display libraries, e.g., as described in U.S. Pat. No. 6,423,538 or a mammalian display library.

Methods for screening display libraries are known in the art. In one example, a display library of the present disclosure is screened using affinity purification, e.g., as described in Scopes (In: Protein purification: principles and practice, Third Edition, Springer Verlag, 1994). Methods of affinity purification typically involve contacting proteins comprising antigen binding domains displayed by the library with a target antigen (e.g., GM-CSF or GM-CSFR) and, following washing, eluting those domains that remain bound to the antigen.

Any variable regions or scFvs identified by screening are readily modified into a complete antibody, if desired. Exemplary methods for modifying or reformatting variable regions or scFvs into a complete antibody are described, for example, in Jones et al., *J Immunol Methods.* 354:85-90, 2010; or Jostock et al., *J Immunol Methods,* 289: 65-80, 2004. Alternatively, or additionally, standard cloning methods are used, e.g., as described in Ausubel et al (In: Current Protocols in Molecular Biology. Wiley Interscience, ISBN 047 150338, 1987), and/or (Sambrook et al (In: Molecular Cloning: Molecular Cloning: A Laboratory Manual, Cold Spring Harbor Laboratories, New York, Third Edition 2001).

Deimmunized, Chimeric, Humanized, Synhumanized, Primatized and Human Proteins

The proteins of the present disclosure may be a humanized protein.

The term "humanized protein" shall be understood to refer to a protein comprising a human-like variable region, which includes CDRs from an antibody from a non-human species (e.g., mouse or rat or non-human primate) grafted onto or inserted into FRs from a human antibody (this type of antibody is also referred to a "CDR-grafted antibody"). Humanized proteins also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, e.g., U.S. Pat. Nos. 5,225,539, 6,054,297, 7,566,771 or 5,585,089. The term "humanized protein" also encompasses a super-humanized protein, e.g., as described in U.S. Pat. No. 7,732,578.

The proteins of the present disclosure may be human proteins. The term "human protein" as used herein refers to proteins having variable and, optionally, constant antibody regions found in humans, e.g. in the human germline or somatic cells or from libraries produced using such regions. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. For the purposes of the present disclosure, a human protein will also be considered to include a protein comprising FRs from a human antibody or FRs comprising sequences from a consensus sequence of human FRs and in which one or more of the CDRs are random or semi-random, e.g., as described in U.S. Pat. Nos. 6,300,064 and/or 6,248,516.

The proteins of the present disclosure may be synhumanized proteins. The term "synhumanized protein" refers to a protein prepared by a method described in WO2007/019620. A synhumanized protein includes a variable region of an antibody, wherein the variable region comprises FRs from a New World primate antibody variable region and CDRs from a non-New World primate antibody variable region. For example, a synhumanized protein includes a variable region of an antibody, wherein the variable region comprises FRs from a New World primate antibody variable region and CDRs from a mouse or rat antibody.

The proteins of the present disclosure may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898.

In one example a protein of the disclosure is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and/or a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331,415; 5,807,715; 4,816,567 and 4,816,397).

The present disclosure also contemplates a deimmunized protein, e.g., as described in WO2000/34317 and WO2004/108158. De-immunized antibodies and proteins have one or more epitopes, e.g., B cell epitopes or T cell epitopes removed (i.e., mutated) to thereby reduce the likelihood that a subject will raise an immune response against the antibody or protein.

Other Proteins Comprising Antibody Variable Regions

The present disclosure also contemplates other proteins comprising a variable region or antigen binding domain of an antibody, such as:

(i) a single-domain antibody, which is a single polypeptide chain comprising all or a portion of the $V_H$ or a $V_L$ of an antibody (see, e.g., U.S. Pat. No. 6,248,516);
(ii) diabodies, triabodies and tetrabodies, e.g., as described in U.S. Pat. No. 5,844,094 and/or US2008152586;
(iii) scFvs, e.g., as described in U.S. Pat. No. 5,260,203;
(iv) minibodies, e.g., as described in U.S. Pat. No. 5,837,821;
(v) "key and hole" bispecific proteins as described in U.S. Pat. No. 5,731,168;
(vi) heteroconjugate proteins, e.g., as described in U.S. Pat. No. 4,676,980;
(vii) heteroconjugate proteins produced using a chemical cross-linker, e.g., as described in U.S. Pat. No. 4,676,980;
(viii) Fab'-SH fragments, e.g., as described in Shalaby et al, *J. Exp. Med.*, 175: 217-225, 1992; or
(ix) $Fab_3$ (e.g., as described in EP19930302894).

Constant Domain Fusions

The present disclosure encompasses a protein comprising a variable region of an antibody and a constant region or Fc or a domain thereof, e.g., $C_H2$ and/or $C_H3$ domain Suitable constant regions and/or domains will be apparent to the skilled artisan and/or the sequences of such polypeptides are readily available from publicly available databases. Kabat et al also provide description of some suitable constant regions/domains.

Constant regions and/or domains thereof are useful for providing biological activities such as, dimerization, extended serum half life e.g., by binding to FcRn (neonatal Fc Receptor), antigen dependent cell cytotoxicity (ADCC), complement dependent cytotoxicity (CDC, antigen dependent cell phagocytosis (ADCP).

The present disclosure also contemplates proteins comprising mutant constant regions or domains, e.g., as described in U.S. Pat. Nos. 7,217,797; 7,217,798; or US20090041770 (having increased half-life) or US2005037000 (increased ADCC).

Stabilized Proteins

Neutralizing proteins of the present disclosure can comprise an IgG4 constant region or a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington DC United States Department of Health and Human Services, 1987 and/or 1991). This position corresponds to position 228 of the hinge region according to the EU numbering system (Kabat et al., Sequences of Proteins of Immunological Interest Washington DC United States Department of Health and Human Services, 2001 and Edelman et al., *Proc. Natl. Acad. USA,* 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional Protein-Based GM-CSFR Signaling Inhibitors

Other proteins that may interfere with the productive interaction of GM-CSF with its receptor include mutant GM-CSF proteins and secreted proteins comprising at least part of the extracellular portion of one or both of the GM-CSF receptor chains that bind to GM-CSF and compete with binding to cell-surface receptor (i.e., soluble GM-CSFRs). For example, a soluble GM-CSF receptor inhibitor can be prepared by fusing the sGM-CSFRα with a Fc region of an antibody. An exemplary soluble GM-CSF receptor is described by Raines et al. *Proc. Natl. Acad. Sci USA* 88: 8203, 1991. An example of a GM-CSFRα-Fc fusion protein is provided, e.g., in Brown et al *Blood* 85: 1488, 1995.

Other GM-CSF signaling inhibitors include GM-CSF mutants. For example, GM-CSF having a mutation of amino acid residue 21 of GM-CSF to Arginine or Lysine (E21R or E221K) described by Hercus et al. *Proc. Natl. Acad. Sci USA* 91:5838, 1994 has been shown to have in vivo activity in preventing dissemination of GM-CSF-dependent leukemia cells in mouse xenograft models.

Immunoglobulins and Immunoglobulin Fragments

An example of a compound of the present disclosure is a protein comprising a variable region of an immunoglobulin, such as a T cell receptor or a heavy chain immunoglobulin (e.g., an IgNAR, a camelid antibody).

Heavy Chain Immunoglobulins

Heavy chain immunoglobulins differ structurally from many other forms of immunoglobulin (e.g., antibodies) in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "$V_{HH}$ domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This means that single domain binding fragments can be derived from heavy chain immunoglobulins, which are easy to express and are generally stable and soluble.

A general description of heavy chain immunoglobulins from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629.

V-Like Proteins

An example of a compound of the disclosure is a T-cell receptor. T cell receptors have two V-domains that combine into a structure similar to the Fv module of an antibody. Novotny et al., *Proc Natl Acad Sci USA* 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a compound of the disclosure is an adnectin. Adnectins are based on the tenth fibronectin type III ($^{10}$Fn3) domain of human fibronectin in which the loop regions are altered to confer antigen binding. For example, three loops at one end of the β-sandwich of the $^{10}$Fn3 domain can be engineered to enable an Adnectin to specifically recognize an antigen. For further details see US20080139791 or WO2005/056764.

Anticalins

In a further example, a compound of the disclosure is an anticalin. Anticalins are derived from lipocalins, which are a family of extracellular proteins which transport small hydrophobic molecules such as steroids, bilins, retinoids and lipids. Lipocalins have a rigid β-sheet secondary structure with a plurality of loops at the open end of the conical structure which can be engineered to bind to an antigen. Such engineered lipocalins are known as anticalins. For further description of anticalins see U.S. Pat. No. 7,250,297B1 or US20070224633.

Affibodies

In a further example, a compound of the disclosure is an affibody. An affibody is a scaffold derived from the Z domain (antigen binding domain) of Protein A of Staphylococcus aureus which can be engineered to bind to antigen. The Z domain consists of a three-helical bundle of approximately 58 amino acids. Libraries have been generated by randomization of surface residues. For further details see EP1641818.

Avimers

In a further example, a compound of the disclosure is an Avimer. Avimers are multidomain proteins derived from the A-domain scaffold family The native domains of approximately 35 amino acids adopt a defined disulphide bonded structure. Diversity is generated by shuffling of the natural variation exhibited by the family of A-domains. For further details see WO2002088171.

DARPins

In a further example, a compound of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Methods for Producing Proteins

Recombinant Expression

In the case of a recombinant protein, nucleic acid encoding same can be cloned into expression vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce an antibody. Exemplary cells used for expressing a protein of the disclosure are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. Nos. 4,816,567 or 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding an antibody (e.g., derived from the information provided herein), an enhancer element, a promoter, and a transcription termination sequence. The skilled artisan will be aware of suitable sequences for expression of an antibody. Exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the antibody may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Protein Purification

Following production/expression, a protein of the disclosure is purified using a method known in the art. Such purification provides the protein of the disclosure substantially free of nonspecific protein, acids, lipids, carbohydrates, and the like. In one example, the protein will be in a preparation wherein more than about 90% (e.g. 95%, 98% or 99%) of the protein in the preparation is a protein of the disclosure.

Standard methods of peptide purification are employed to obtain an isolated protein of the disclosure, including but not limited to various high-pressure (or performance) liquid chromatography (HPLC) and non-HPLC polypeptide isolation protocols, such as size exclusion chromatography, ion exchange chromatography, hydrophobic interaction chromatography, mixed mode chromatography, phase separation methods, electrophoretic separations, precipitation methods, salting in/out methods, immunochromatography, and/or other methods.

In one example, affinity purification is useful for isolating a fusion protein comprising a label. Methods for isolating a protein using affinity chromatography are known in the art and described, for example, in Scopes (In: Protein purification: principles and practice, Third Edition, Springer Verlag, 1994). For example, an antibody or compound that binds to the label (in the case of a polyhistidine tag this may be, for example, nickel-NTA) is immobilized on a solid support. A sample comprising a protein is then contacted to the immobilized antibody or compound for a time and under conditions sufficient for binding to occur. Following washing to remove any unbound or non-specifically bound protein, the protein is eluted.

In the case of a protein comprising a Fc region of an antibody, protein A or protein G or modified forms thereof can be used for affinity purification. Protein A is useful for isolating purified proteins comprising a human γ1, γ2, or γ4 heavy chain Fc region. Protein G is recommended for all mouse Fc isotypes and for human γ3.

Nucleic Acid-Based GM-CSFR Signaling Inhibitors

In one example of the disclosure, therapeutic and/or prophylactic methods as described herein according to any example of the disclosure involve reducing expression of GM-CSF and/or CM-CSFR. For example, such a method involves administering a compound that reduces transcription and/or translation of the nucleic acid. In one example, the compound is a nucleic acid, e.g., an antisense polynucleotide, a ribozyme, a PNA, an interfering RNA, a siRNA, a microRNA Antisense Nucleic Acids The term "antisense nucleic acid" shall be taken to mean a DNA or RNA or derivative thereof (e.g., LNA or PNA), or combination thereof that is complementary to at least a portion of a specific mRNA molecule encoding a polypeptide as described herein in any example of the disclosure and capable of interfering with a post-transcriptional event such as mRNA translation. The use of antisense methods is known in the art (see for example, Hartmann and Endres (editors), Manual of Antisense Methodology, Kluwer (1999)).

An antisense nucleic acid of the disclosure will hybridize to a target nucleic acid under physiological conditions. Antisense nucleic acids include sequences that correspond to structural genes or coding regions or to sequences that effect control over gene expression or splicing. For example, the antisense nucleic acid may correspond to the targeted coding region of a nucleic acid encoding GM-CSF or GM-CSFR, or the 5'-untranslated region (UTR) or the 3'-UTR or combination of these. It may be complementary in part to intron sequences, which may be spliced out during or after transcription, for example only to exon sequences of the target gene. The length of the antisense sequence should be at least 19 contiguous nucleotides, for example, at least 50 nucleotides, such as at least 100, 200, 500 or 1000 nucleotides of a nucleic acid encoding GM-CSF or GM-CSFR. The full-length sequence complementary to the entire gene transcript may be used. The length can be 100-2000 nucleotides. The degree of identity of the antisense sequence to the targeted transcript should be at least 90%, for example, 95-100%.

Catalytic Nucleic Acid

The term "catalytic nucleic acid" refers to a DNA molecule or DNA-containing molecule (also known in the art as a "deoxyribozyme" or "DNAzyme") or a RNA or RNA-containing molecule (also known as a "ribozyme" or "RNAzyme") which specifically recognizes a distinct substrate and catalyses the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are useful in this disclosure are a hammerhead ribozyme and a hairpin ribozyme.

RNA Interference

RNA interference (RNAi) is useful for specifically inhibiting the production of a particular protein. Without being limited by theory, this technology relies on the presence of dsRNA molecules that contain a sequence that is essentially identical to the mRNA of the gene of interest or part thereof, in this case an mRNA encoding a GM-CSF or GM-CSFR. Conveniently, the dsRNA can be produced from a single promoter in a recombinant vector host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present disclosure is well within the capacity of a person skilled in the art, particularly considering WO99/32619, WO99/53050, WO99/49029, and WO01/34815.

The length of the sense and antisense sequences that hybridize should each be at least 19 contiguous nucleotides, such as at least 30 or 50 nucleotides, for example at least 100, 200, 500 or 1000 nucleotides. The full-length sequence corresponding to the entire gene transcript may be used. The lengths can be 100-2000 nucleotides. The degree of identity of the sense and antisense sequences to the targeted transcript should be at least 85%, for example, at least 90% such as, 95-100%.

Exemplary small interfering RNA ("siRNA") molecules comprise a nucleotide sequence that is identical to about 19-21 contiguous nucleotides of the target mRNA. For example, the siRNA sequence commences with the dinucleotide AA, comprises a GC-content of about 30-70% (for example, 30-60%, such as 40-60% for example about 45%-55%), and does not have a high percentage identity to any nucleotide sequence other than the target in the genome of the mammal in which it is to be introduced, for example as determined by standard BLAST search.

Short hairpin RNA (shRNA) that reduce expression of GM-CSFR are also known in the art and described, for example, in Volmar et al., *Cytokine.* 42:336-44, 2008. Such shRNA are commercially available from, for example, Origene Technologies, Inc.

Screening Assays

Compounds that inhibit GM-CSF signaling can be identified using techniques known in the art, e.g., as described below Similarly, amounts of GM-CSF signaling inhibitors suitable for use in a method described herein can be determined or estimated using techniques known in the art, e.g., as described below.

Neutralization Assays

For proteins that bind to GM-CSF or GM-CSFR and inhibit signaling, a neutralization assay can be used.

In one example, a neutralization assay involves contacting a soluble GM-CSFR with a compound in the presence or absence of detectably labeled GM-CSF. The level of GM-CSF bound to the soluble GM-CSFR is then assessed. A reduced level of bound labeled GM-CSF in the presence of the compound compared to in the absence of the compound indicates the compound inhibits GM-CSF binding to GM-CSFR and, as a consequence GM-CSF signaling. In one example, a neutralization assay is performed as described in Urano et al., *J. Vis. Exp.* 52, e2742, 2011.

A reciprocal assay can be used using labeled soluble GM-CSFR.

In another example, a compound that inhibits GM-CSF signaling is identified using a cell dependent on GM-CSF signaling for proliferation, e.g., a bone marrow cell or a TF-1 cell. Cells are cultured in the presence of GM-CSF and in the presence or absence of a compound. Cell proliferation is then assessed using standard methods, e.g., colony formation assays, thymidine incorporation or uptake of another suitable marker of cell proliferation. A compound that reduces the level of proliferation in the presence of GM-CSF is considered an inhibitor of GM-CSF signaling.

The present disclosure contemplates additional assays for determining inhibitors of GM-CSF signaling. For example, neutrophil migration to N-formyl-methionine-leucine-phenylalanine or Leukotriene B4 is induced by GM-CSF and a compound that reduces or prevents such migration is considered an inhibitor of GM-CSF.

Compounds can also be assessed for their ability to bind to GM-CSF and/or GM-CSFR using standard methods. Methods for assessing binding to a protein are known in the art, e.g., as described in Scopes (In: Protein purification: principles and practice, Third Edition, Springer Verlag, 1994). Such a method generally involves labeling the compound and contacting it with immobilized GM-CSF, GM-CSFR or soluble GM-CSFR. Following washing to remove non-specific bound compound, the amount of label and, as a consequence, bound compound is detected. Of course, the compound can be immobilized and the GM-CSF, GM-CSFR or soluble GM-CSFR labeled. Panning-type assays can also be used. Alternatively, or additionally, surface plasmon resonance assays can be used.

Expression Assays

A compound that reduces or prevents expression of GM-CSF or GM-CSFR is identified by contacting a cell with the compound and determining the level of expression of the GM-CSF or GM-CSFR. Suitable methods for determining gene expression at the nucleic acid level are known in the art and include, for example, quantitative polymerase chain reaction (qPCR) or microarray assays. Suitable methods for determining expression at the protein level are also known in the art and include, for example, enzyme-linked immunosorbent assay (ELISA), fluorescence linked immunosorbent assay (FLISA), immunofluorescence or Western blotting.

In Vivo Assays

Compounds of the present disclosure can also be assessed for therapeutic efficacy in an animal model of IBD.

For example, the compound is administered to a model of IBD, such as:

- a spontaneous model of IBD, e.g., cotton-top tamarin colitis;
- colitis induced by acetic acid, dextran sulfate sodium or indomethacin
- an adoptive transfer model, e.g., adoptive transfer of $CD45RB^{high}$ cells (e.g., Kanai et al., *Inflamm Bowel Dis.,* 12: 89-99, 2006); or
- a genetically modified model, e.g., IL-10 knockout or TCR-alpha chain knockout mice.

In another example, the compound is administered to an animal that has been administered an agonistic anti-CD40 antibodies. Administration of such antibodies induces inflammation in the intestine modeling IBD (Uhlig et al., *Immunity* 25: 309-318, 2006).

Pharmaceutical Compositions and Methods of Treatment

A compound that inhibits GM-CSF signaling (syn. active ingredient) is useful for parenteral, topical, oral, or local administration, aerosol administration, or transdermal administration, for prophylactic or for therapeutic treatment. In one example, the compound is administered parenterally, such as subcutaneously or intravenously.

Formulation of a compound to be administered will vary according to the route of administration and formulation (e.g., solution, emulsion, capsule) selected. An appropriate pharmaceutical composition comprising compound to be administered can be prepared in a physiologically acceptable carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The compound can be lyophilized for storage and reconstituted in a suitable carrier prior to use according to art-known lyophilization and reconstitution techniques.

The optimum concentration of the active ingredient(s) in the chosen medium can be determined empirically, according to procedures known to the skilled artisan, and will depend on the ultimate pharmaceutical formulation desired.

The dosage ranges for the administration of the compound of the disclosure are those large enough to produce the desired effect. For example, the composition comprises a therapeutically or prophylactically effective amount of the compound.

As used herein, the term "effective amount" shall be taken to mean a sufficient quantity of the compound to inhibit/reduce/prevent signaling of GM-CSF in a subject. The skilled artisan will be aware that such an amount will vary depending on, for example, the compound and/or the particular subject and/or the type or severity of IBD being treated. Accordingly, this term is not to be construed to limit the disclosure to a specific quantity, e.g., weight or number of compounds.

As used herein, the term "therapeutically effective amount" shall be taken to mean a sufficient quantity of compound to reduce or inhibit one or more symptoms of an IBD.

As used herein, the term "prophylactically effective amount" shall be taken to mean a sufficient quantity of compound to prevent or inhibit or delay the onset of one or more detectable symptoms of an IBD.

In one example, a compound is administered in an amount sufficient to inhibit or prevent a local or systemic innate immune response. An innate immune response can be detected by obtaining a sample from a subject and detecting the number of a population of innate immune cells therein, e.g. dendritic cells, macrophages, natural killer cells, neutrophils or γδ T cells. The number of cells can be determined using, e.g., flow cytometry or immunohistochemistry or immunofluorescence (e.g., dendritic cells express CD86 or CD83, macrophages express CD14 or CD68, natural killer cells express CD16, neutophils express CD18 or CD11b and γδ T cells express CD1d). To determine a systemic innate immune response, the number of cells in a blood sample or plasma sample can be determined To determine a local innate immune response, the number of cells in a sample from, for example, an intestine of a subject can be determined.

An innate immune response can be detected by obtaining a sample from a subject and detecting cytokines produced by innate immune cells therein. Exemplary cytokines include interleukin-1, interleukin-6, interleukin-8, interleukin-12, interleukin-15, interleukin-18, tumor necrosis factor a or type 1 interferon. These cytokines are readily determined using standard methods, e.g., ELISA, FLISA or ELISPOT assays.

The foregoing paragraphs do not mean that each time a subject is treated, the presence or severity of a local or systemic innate immune response must be assessed. Such an immune response need not even be assessed in some subjects. Rather, once a suitable dose has been determined in a population of subjects (i.e., that has been shown to inhibit or prevent a local or systemic innate immune response in the majority of the population), it is sufficient to administer that amount to a subject.

The dosage should not be so large as to cause adverse side effects, such as hyper viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

Dosage can vary from about 0.1 mg/kg to about 300 mg/kg, e.g., from about 0.2 mg/kg to about 200 mg/kg, such as, from about 0.5 mg/kg to about 20 mg/kg, in one or more dose administrations daily, for one or several days.

In some examples, the compound is administered at an initial (or loading) dose which is higher than subsequent (maintenance doses). For example, the compound is administered at an initial dose of between about 1 mg/kg to about 30 mg/kg. The compound is then administered at a maintenance dose of between about 0.0001 mg/kg to about 1 mg/kg. The maintenance doses may be administered every 7-35 days, such as, every 14 or 21 or 28 days.

In some examples, a dose escalation regime is used, in which a compound is initially administered at a lower dose than used in subsequent doses. This dosage regime is useful in the case of subject's initially suffering adverse events In the case of a subject that is not adequately responding to treatment, multiple doses in a week may be administered. Alternatively, or in addition, increasing doses may be administered.

A subject may be retreated with the compound, by being given more than one exposure or set of doses, such as at least about two exposures of the compound, for example, from about 2 to 60 exposures, and more particularly about 2 to 40 exposures, most particularly, about 2 to 20 exposures.

In one example, any retreatment may be given when signs or symptoms of disease return, when the subject is no longer in remission, and/or when autoantibody levels (e.g., p-ANCA or anti-hTM5 autoantibody levels) rise.

In another example, any retreatment may be given at defined intervals. For example, subsequent exposures may be administered at various intervals, such as, for example, about 24-28 weeks or 48-56 weeks or longer. For example, such exposures are administered at intervals each of about 24-26 weeks or about 38-42 weeks, or about 50-54 weeks.

One or more compounds of the present disclosure can be administered to an individual by an appropriate route, either alone or in combination with (before, simultaneous with, or after) another drug or agent. For example, the compound of the present disclosure can also be used in combination with other compounds used in the treatment of IBD, e.g., a TNF antagonist (such as, infliximab, etanercept, adalimumab), an anti-CD20 antibody (e.g., rituximab), an interferon (such as interferon-alpha, interferon-beta-1a or interferon-beta-1b), an oligopeptide such as glatiramer acetate, an agent blocking CD40-CD40 ligand, a cytotoxic agent (such as mitoxantrone, methotrexate, cyclophosphamide, chlorambucil, leflunomide, or azathioprine), one or more immunosuppressive agents (e.g. azathioprine, 6-mercaptopurine, cyclosporine), an alpha 4 integrin antibody such as natalizumab, a steroid such as corticosteroid (e.g., methylprednisolone, prednisone, dexamethasone, or glucocorticoid).

Exemplary additional medicaments include one, two, three or four of: an aminosalicylate, an oral corticosteroid, 6-mercaptopurine (6-MP) or azathioprine.

Combined treatment herein includes co-administration, using separate formulations or a single pharmaceutical formulation, and consecutive administration in either order, wherein, for example, there is a time period while both (or all) active agents simultaneously exert their biological activities.

Kits

Another example of the disclosure provides kits containing compounds useful for the treatment of an IBD as described above.

In one example, the kit comprises (a) a container comprising a compound that inhibits GM-CSF signaling as described herein, optionally in a pharmaceutically acceptable carrier or diluent; and (b) a package insert with instructions for treating a IBD in a subject.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for treating the IBD and may have a sterile access port (for example, the container may be an intravenous solution bag or a vial having a stopper pierceable by a hypodermic injection needle). At least one active agent in the composition is the compound that inhibits GM-CSF signaling. The label or package insert indicates that the composition is used for treating a subject eligible for treatment, e.g., one having or predisposed to IBD, with specific guidance regarding dosing amounts and intervals of compound and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The kit optionally further comprises a container comprises a second medicament, wherein the compound that inhibits GM-CSF signaling is a first medicament, and which article further comprises instructions on the package insert for treating the subject with the second medicament, in an effective amount. The second medicament may be any of those set forth above, with an exemplary second medicament being an aminosalicylate, an oral corticosteroid, 6-mercaptopurine (6-MP), and azathioprine.

The present disclosure includes the following non-limiting Examples.

EXAMPLE 1

Treatment of IBD with a GM-CSF Signaling Inhibitor

IBD was induced in mice using an agonistic anti-CD40 antibody, substantially as described in Uhlig et al., *Immunity* 25: 309-318, 2006. In summary, mice were treated with intraperitoneally with 125 μg of the anti-CD40 agonist mAb FGK45. Animals were also treated intraperitoneally with 200 μg of either isotype control (IgG2a) or anti-GM-CSF antibody (MP122E9 from R&D Systems) on day −1 (i.e., 1 day before inducing IBD) and 2 and 5 days after inducing IBD. Weight was monitored daily. At day 7 animals were killed and colons removed for histology and scored substantially as previously described (Uhlig et al., supra.).

Figure 1B:
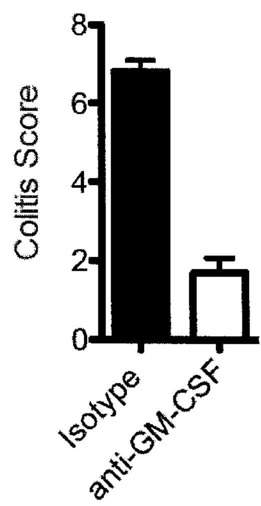
FIG. 1B is a graphical representation showing histological colitis scores based on sections of colon from treated animals as described in respect of FIG. 1A.

As shown in FIG. 1A, treatment with anti-GM-CSF antibody reduced the amount of weight lost by animals suffering from IBD. FIG. 1B shows that the severity of colitis induced in animals treated with anti-GM-CSF antibody was substantially reduced compared to animals treated with isotype control antibody.

The invention claimed is:

1. A method for treating an inflammatory bowel disease (IBD) in a subject in need thereof, the method comprising administering to the subject an effective amount of an antibody that specifically binds GM-CSF or GM-CSFR, wherein said antibody inhibits granulocyte-macrophage colony stimulating factor (GM-CSF) signaling and treats IBD in the subject.

2. The method of claim 1, wherein the IBD is characterized by an innate immune response in the digestive system.

3. The method of claim 1, wherein the IBD is characterized by a systemic innate immune response.

4. The method of claim 1, wherein the IBD is characterized by a CD40-mediated immune response.

5. The method of claim 1, wherein the IBD is Crohn's disease.

6. The method of claim 1, wherein the antibody is administered in an amount sufficient to inhibit an innate immune response in the digestive system and/or a systemic innate immune response.

7. The method of claim 1 additionally comprising administering a further compound to treat the IBD.

8. A method for treating an inflammatory bowel disease (IBD) in a subject in need thereof, the method comprising administering to the subject an effective amount of a protein that specifically binds GM-CSF or GM-CSFR, wherein said protein is selected from the group consisting of: (i) a GM-CSF-binding protein comprising an antibody variable region that specifically binds GM-CSF and neutralizes GM-CSF-signaling, and (ii) a GM-CSFR-binding protein comprising an antibody variable region that specifically binds GM-CSFR and neutralizes GM-CSF-signaling.

9. The method of claim 8, wherein the protein that specifically binds GM-CSF or GM-CSFR is selected from the group consisting of:

(i) a single chain Fv fragment (scFv);
(ii) a dimeric scFv (di-scFv);
(iv) a diabody;
(v) a triabody;
(vi) a tetrabody;
(vii) a Fab;
(viii) a $F(ab')_2$;
(ix) a Fv; and
(x) one of (i) to (ix) linked to a constant region of an antibody, Fc or a heavy chain constant domain ($C_H$) 2 and/or $C_H$3.

10. The method of claim 8, wherein the protein is recombinant, chimeric, CDR grafted, humanized, humaneered, synhumanized, primatized, deimmunized or human.

* * * * *